United States Patent [19]

Bracken

[11] Patent Number: Plant 5,520

[45] Date of Patent: Jul. 23, 1985

[54] MAGNOLIA GRANDIFLORA NAMED BRACKENS BROWN BEAUTY

[75] Inventor: Ray Bracken, Piedmont, S.C.

[73] Assignee: Ray Bracken Nursery, Inc., Piedmont, S.C.

[21] Appl. No.: 564,886

[22] Filed: Dec. 23, 1983

[51] Int. Cl.[3] ..... A01H 5/00

[52] U.S. Cl. ..... Plt./51

[58] Field of Search ..... Plt./51

*Primary Examiner*—Robert E. Bagwill

*Attorney, Agent, or Firm*—Chas. W. Rummler

[57] ABSTRACT

A new Southern magnolia of the grandiflora variety distinguished by a rapid growth rate and an abundant branch and foliage development which maintains a very dense habit from ground to almost the very top producing a compact pyramidal-oval crown, the abundant foliage being particularly distinguished by the yellow-green coloring of the new leaves which change to dark green at maturity and all of which have a rusty brown pubescence on the under side which affords a distinctive green and brown coloration for the entire tree. This new magnolia grandiflora is further distinguished by its profuse production of creamy white flowers which are half the size or less than those of the species and produce fruit that is about half the size of the fruit normal to the species.

3 Drawing Figures

BACKGROUND OF THE NEW PLANT

My new variety of magnolia grandiflora was discovered by me in 1968 as a seedling originated in a bed of about 2500 seedling grown South magnolias at my nursery in Easley, S.C. The original seeds for this bed of Southern magnolias resulted from open pollination of a number of Southern magnolias and the discovery of this new variety was brought about by reason of the apparently novel and distinctive features of the plant which presented a new and improved combination of characteristics never before exhibited in any Southern magnolia of which I have ever been aware.

I reproduced this new variety of magnolia tree by means of cuttings at my nursery at Easley, S.C., and a considerable number of selected cuttings were rooted and grown to test the stability of the novel characteristics observed in the original plant. During the years since my discovery of this variety, it has been propagated through several successive generations and I was able to thereby determine that the novel and distinctive features of my new magnolia variety remained true from generation to generation and appeared to be firmly fixed.

DESCRIPTION OF THE DRAWINGS

My new magnolia grandiflora, and certain features thereof, are illustrated by the accompanying drawings, of which sheet one shows a tree that is about seven years old and about ten to twelve feet tall, and sheet two shows front and back sides of a young leaf in the upper view and the front and back sides of a mature leaf in the lower view, the front side being at the left and the colors being as close to those specified as is reasonably possible to obtain by conventional photographic procedures.

DESCRIPTION OF THE NEW PLANT

The following is a detailed description of my new magnolia grandiflora based upon observations of a tree growing in my nursery and about seven years old, the observations having been made in the early summer of 1983 at Easley, S.C., the color designations being according to The R.H.S. Colour Chart of The Royal Horticultural Society of London, England.

Origin: Seedling.

Parentage: Unknown. This seedling originated in a bed of seedling grown Southern magnolias, the original seeds for this bed resulting from open pollination of a number of Southern magnolias.

Classification:

*Botanic.*—Magnolia Grandiflora.

*Commercial.*—Southern Magnolia.

Form: Tall evergreen tree of pyramidal habit with a straight and strong central trunk.

Height: In a period of seven years from a rooted cutting, the plant reaches a height of ten to twelve feet with a trunk size of about three to four inches and with smooth grey-brown bark which becomes deep grey with maturity. The growth rate is normally about 20 or more inches per year, ultimately reaching a height of 50 to 60 feet at maturity, yet the plant maintains a dense habit because of its abundant branch development.

Branching: Numerous and closely spaced diverging at an angle of approximately 45° from the central trunk. The branches sweep back toward the trunk, however, and grow almost parallel for a distance creating a dense, compact crown which is totally atypical for a young Southern magnolia, although fifteen year old plants have maintained this same secondary branching orientation. The development of five to seven secondary branches in a growth flush results in a very dense, compact plant all the way to ground level. In Easley, S.C., a second flush of growth develops from the first flush in July yielding four to five additional breaks which in a single growing season may mean as many as twenty to thirty-five breaks.

Foliage: The leaves are evergreen and alternate, firmly coriaceous in texture and of obovate-oblong or elliptical shape, the size being from four to seven and one-half inches long and two to three inches wide with entire margins and undulating surface. The petioles are stout, pubescent, and about one-half to one inch long.

Color:

*New growth.*—Top Surface — Yellow Green R.H.S. 144 A. Bottom Surface — Greyed Orange R.H.S. 165 B.

*Mature leaves.*—Top Side — Dark Green R.H.S. 137 B. Bottom Side — Grey Brown R.H.S. 199 A. Color changes occur as the leaves mature and the time of change depends on climatic conditions. In South Carolina, the leaves from two growth flushes have matured to lustrous dark green by late August.

Stems: Young stems, one and two years old, are stout and strong, one-quarter inch to three-eighths inch in diameter, pubescent, rust colored and dotted with grey brown lenticels marked with a distinct circular scale scar at each node. Older stems show a greenish brown coloration as the rusty pubescence falls away.

Buds: Buds that are terminal of the stem are large, about one inch long, slightly curved, and covered by a single ensheathing scale which has a rusty brown silky pubescence. Lateral buds are smaller, about one-eighth inch long, borne singly above the leaf scar, ovoid in shape and with brownish pubescence.

Flowers: Each flower is borne singly at the end of a branch, is about four inches in diameter, and is composed of nine petals that are tightly overlapping in bud and open to a cup-shaped configuration. The flower color is creamy white and very pleasingly fragrant. Flowering is initiated in mid to late May and continuous into early July on a sustained basis, after which sporadic flowers occur throughout the growing season.

Fruit: The fruit is aggregate of follicles that are ovoid in shape and borne singly at the end of the branch, each averaging about two to two and one-half inches long and one to one and one-half inches wide. The fruits turn rose pink to rose red in early September and remain colorful into October; the seeds are oval in shape and are one-quarter to three-eighths inch long covered with a red aril. They naturally dehisce from the follicles in September–October and are attached by a string-like funicular stalk.

In general, the outstanding characteristics of my new variety of magnolia grandiflora, which distinguish it from other varieties of Southern magnolia and all others, reside in its overall very dense and pyramidal appearance enlightened by the light green color of its new leaves that changes to a lustrous dark green color at maturity. The young leaves have a brownish under side which becomes rusty brown as the leaves mature and the combination of the light and dark green leaves with the brownish under side coloring provides a very attractive and pleasing color variegation for the overall and almost solid appearance of the entire tree. The four inch diameter creamy white flowers are very much smaller than the eight to twelve inch normal flower of the species and the flowers are borne in the first and second year of growth on plants grown from cuttings. In the fifth and sixth year, the plant displays extreme floriferous qualities and is infinitely superior to plants grown from seed which may take as long as fifteen to twenty years to flower.

The fruit is about half the size and is not as obtrusive or messy as the relatively large fruit of the species. The compact, pyramidal-oval crown of my new magnolia selection is more upright than is typical of most Southern magnolias which tend to a more broad-pyramid and more open crown, especially in youth. Also, the straight central trunk, even in youth, strongly supports the secondary branches and results in a tree that requires no staking.

My new magnolia grandiflora is easy to root from cuttings collected in July and early August which assures trueness-to-type and the rapid growth rate under normal fertilizer and moisture conditions, together with its very abundant branch development, assures that the plant will always maintain a very dense habit.

I claim:

1. The new and distinct variety of magnolia grandiflora, substantially as herein shown and described, characterized by its vigorous, dense, pyramidal growth habit and its abundant production of small, white, very fragrant flowers and rose red fruits which are half the size of those normal to the species.

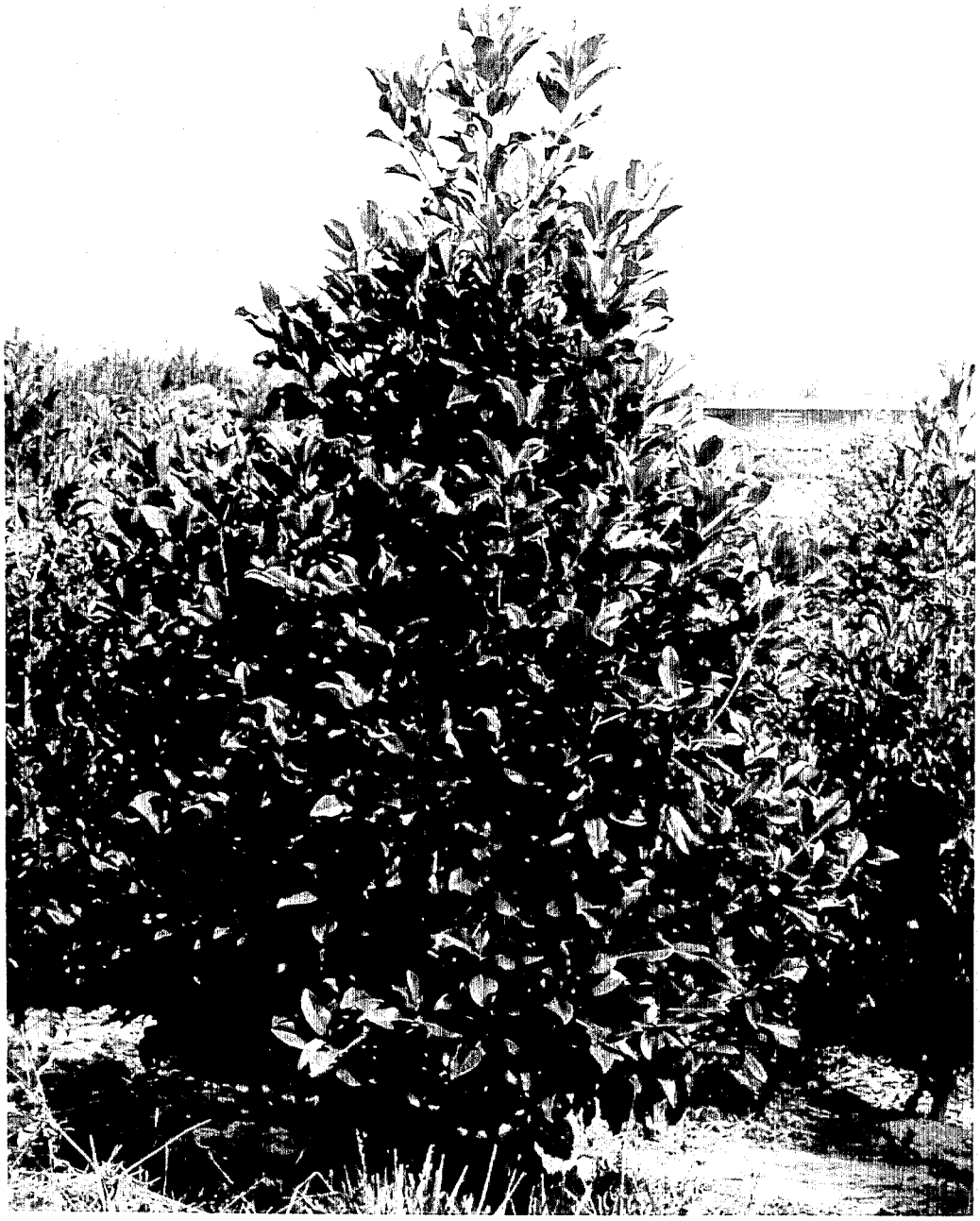

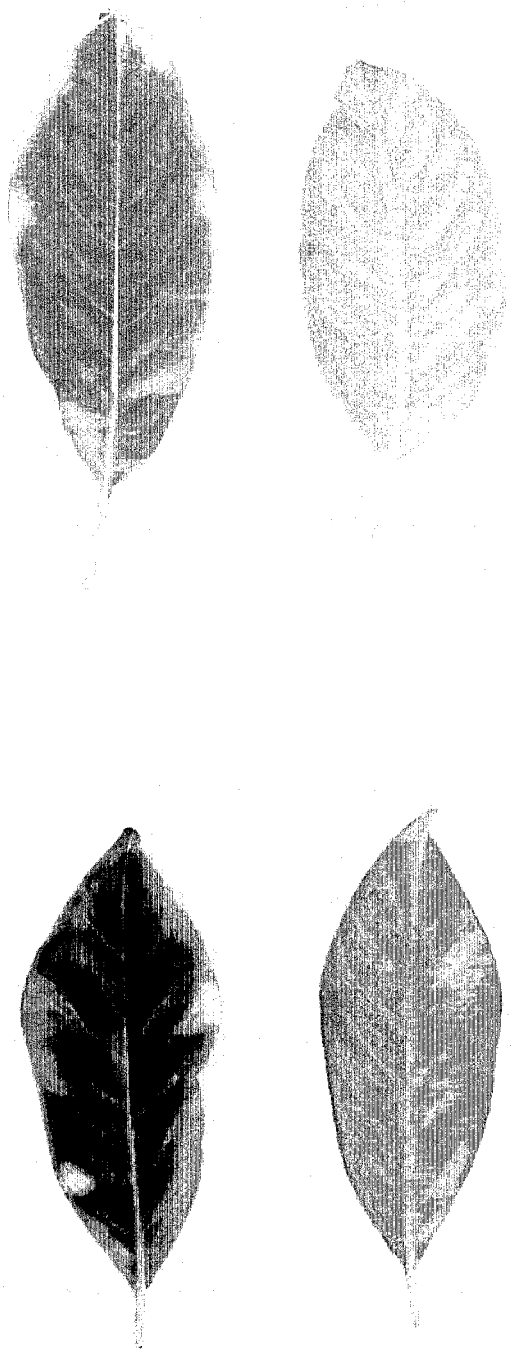

* * * * *